United States Patent [19]
Müller

[11] Patent Number: 5,824,478
[45] Date of Patent: Oct. 20, 1998

[54] DIAGNOSTIC METHODS AND PROBES

[75] Inventor: Uwe Richard Müller, Plano, Ill.

[73] Assignee: Vysis, Inc., Downers Grove, Ill.

[21] Appl. No.: 643,109

[22] Filed: Apr. 30, 1996

[51] Int. Cl.$^6$ .............................. C12Q 1/68; G01N 33/53; G01N 33/566
[52] U.S. Cl. ................................ 435/6; 435/7.1; 436/501
[58] Field of Search .................................. 435/6, 7.1, 7.5, 435/7.72, 7.9, 7.94, 183; 436/94, 501, 800; 536/24.3, 24.31, 24.32, 23.1; 935/78, 76, 77

[56] References Cited

U.S. PATENT DOCUMENTS

| | | | |
|---|---|---|---|
| 4,868,105 | 9/1989 | Urdea et al. | 435/6 |
| 4,874,492 | 10/1989 | Mackay | 204/182.8 |
| 4,946,778 | 8/1990 | Ladner et al. | 435/69.6 |
| 5,068,175 | 11/1991 | Prashad | 435/6 |
| 5,118,605 | 6/1992 | Urdea | 435/6 |
| 5,132,405 | 7/1992 | Huston et al. | 530/387.3 |
| 5,270,184 | 12/1993 | Walker et al. | 435/91.1 |
| 5,318,680 | 6/1994 | Fishman et al. | 204/180.1 |
| 5,324,401 | 6/1994 | Yeung et al. | 204/180.1 |
| 5,324,632 | 6/1994 | Weisberg et al. | 435/6 |
| 5,348,633 | 9/1994 | Karger et al. | 204/180.1 |
| 5,376,249 | 12/1994 | Afeyan et al. | 204/180.1 |
| 5,424,413 | 6/1995 | Hogan et al. | 536/23.31 |
| 5,571,398 | 11/1996 | Karger et al. | 204/603 |
| 5,593,824 | 1/1997 | Treml et al. | 435/4 |
| 5,608,039 | 3/1997 | Pastan et al. | 530/387.3 |
| 5,635,352 | 6/1997 | Urdea et al. | 435/6 |

FOREIGN PATENT DOCUMENTS

| | | | |
|---|---|---|---|
| 622464A2 | 11/1994 | European Pat. Off. | C12Q 1/68 |
| 703296A1 | 3/1996 | European Pat. Off. | C12Q 1/68 |

OTHER PUBLICATIONS

Beattie et al., Advances in Genosensor Research, Clinical Chemistry. 41:700–706 (1995).
Beattie et al., Genosensor Technology, Clinical Chemistry 39:719–722, 1993.
Drysdale and Righetti, Fractionation of Nucleic Acids by Isoelectric Focusing, Biochemistry 11:4044–4052, 1972.
Drysdale, Fractionation of Nucleic Acids on Isoelectric Focusing, Proceed. Int. Symp. Electrofocusing—Isoelectrophoresis, (1976) 241–52.
Maskos and Southern, Oligonucleotide Hybridisations on Glass Supports: A Novel Linker for Oligonucleotide Synthesis . . . Properties of Oligonucleotides Synthesised in situ, Nucleic Acids Research 20:1679–1684, 1992.
Novotny et al., Recent advances in capillary electrophoresis of proteins, peptides and amino acids, Electrophoresis 11:735–749, 1990.
Polushin and Cohen, Antisense Pro–drugs: 5'–ester Oligodeoxynucleotides, Nucleic Acids Research 22:5492–5496, 1994.
Ranki et al., Sandwich Hybridization as a Convenient Method for the Detection of Nucleic Acids in Crude Samples, Gene 21:77–85, 1983.
Righetti and Drysdale, Small–scale Fractionation of Proteins and Nucleic Acids by Isoelectric Focusing in Polyacrylamide Gels, Annals New York Academy of Sciences 209:163–185, 1973.
Sova et al., Isoelectric Focusing Analysis of Monoplasmids Carried by *Escherichia Coli* Strains, Int. Symposium Antibiotics Resistance, 1979.
Matthews et al., Analytical Biochemistry 169:1–25 (1988).

*Primary Examiner*—W. Gary Jones
*Assistant Examiner*—Ethan Whisenant
*Attorney, Agent, or Firm*—Norval B. Galloway

[57] ABSTRACT

The invention features methods for detecting a target analyte in a sample. In these methods, a sample is contacted with a detector probe and a capture probe to form a detector probe-analyte-capture probe complex. The detector probe includes a new moiety, having a predetermined pI and containing a detectable label. The complex is isolated from detector probe that is not bound in the complex, the moiety is released from the complex, and the released moiety is concentrated, e.g., by isoelectric focusing or other methods. Detection of the moiety, e.g., at a position in a pH gradient corresponding to its pI, can be used as a measure of the presence and concentration of the analyte in the sample.

32 Claims, 1 Drawing Sheet

SEQUENCE LISTING ( 1 ) GENERAL INFORMATION:

( i i i ) NUMBER OF SEQUENCES: 1

( 2 ) INFORMATION FOR SEQ ID NO: 1:

( i ) SEQUENCE CHARACTERISTICS:
        ( A ) LENGTH: 28
        ( B ) TYPE: nucleic acid
        ( C ) STRANDEDNESS: single
        ( D ) TOPOLOGY: linear ( x i ) SEQUENCE DESCRIPTION: SEQ ID NO: 1:

AGCTCACAGC ATATGCGCTT TTGTGTAC       2 8

DIAGNOSTIC METHODS AND PROBES

STATEMENT AS TO FEDERALLY SPONSORED RESEARCH

This invention was supported in part by the U.S. Government under Advanced Technology Program project number 95-08-0012 and cooperative agreement number 70NANB5H1108, awarded by the Department of Commerce, and administered by the National Institute of Standards and Technology. The Government has certain rights in the invention.

BACKGROUND OF THE INVENTION

This invention relates to methods and probes for detecting a target analyte in a sample.

Detection of analytes present in trace amounts in a sample requires sensitive and specific methods. Otherwise, detection of such analytes may be hindered by the presence of substances found at higher concentrations in the sample. This problem is compounded if the analyte does not have a physical or chemical property that renders it easy to detect.

Isoelectric focusing (IEF) is an electrophoretic method in which an electric field is applied to a molecule in a pH gradient to localize the molecule to a position in the gradient at which its net charge is zero, i.e., at its isoelectric point (pI). IEF is often used to fractionate proteins in complex mixtures and as a tool for characterizing biomolecules of unknown composition. The pH gradients used in IEF are commercially available, and consist of mixtures of multi-charged ampholytes, which are low molecular weight compounds (e.g., polyaminopolycarboxylic acids) having closely spaced, known pI values and high conductivity. The mixture of ampholytes forms a pH gradient upon application of an electric field.

Capillary tubes have been used in various electrophoretic methods, including IEF (see, e.g., Novotny et al., Electrophoresis, 11:735–749, 1990). One application of capillary IEF has been for detecting target analytes in samples. For example, Afeyan et al., U.S. Pat. No. 5,376,249 (1994), describes a method in which a complex formed between an analyte and a labeled analyte-specific binding moiety is fractionated by capillary IEF. Similarly, Karger et al., U.S. Pat. No. 5,348,633 (1994), describes a method in which a complex formed between an analyte and a labelled Fab fragment of an immunoglobulin is concentrated by capillary IEF. In both of these methods, the pI of an analyte-probe complex for each analyte to be detected must be determined empirically. If there are more than a few analytes, this empirical determination can become difficult.

SUMMARY OF THE INVENTION

The present invention is based on the discovery that a new detectable and isolable moiety can be used in simple methods to detect a wide variety of analytes in complex samples. The special moiety is bound to a probe that specifically binds to the targeted analyte, the sample is mixed with the analyte-specific probe, the probe is bound to the analyte to form an analyte-probe complex, unbound probe is removed from the complex, and the moiety is released from the complex and isolated, e.g., by fractionation in a pH gradient by IEF. Detection of the moiety, e.g., at the position in the gradient corresponding to its pI, is used as a measure of the presence of the analyte in the sample.

Accordingly, in one aspect, the invention features a method for detecting an analyte in a sample. In this method, the sample is contacted with a detector probe, which contains a moiety (e.g., phycoerythrin) containing a detectable label, and a capture probe to form a detector probe-analyte-capture probe complex. The complex is then separated from any detector probe that is not bound in the complex, the moiety is released from the complex, the released moiety is isolated from the complex, and, optionally, concentrated. The isolated moiety can then be detected as a measure of the presence of the analyte in the sample.

In addition to the detectable label, the moiety has a property, e.g., a predetermined pI, that facilitates its isolation and/or concentration. In the case where the moiety has a predetermined pI, the isolating and concentrating of the released moiety can be carried out by isoelectric focusing. The focused moiety can then be detected at a position in a pH gradient corresponding to the pi of the moiety, as a measure of the presence of the analyte in the sample. The moiety may also be isolated and/or concentrated on the basis of size, e.g., by the use of column chromatography or a molecular sieve.

The sample, detector probe, and capture probe can be contacted with one another in any order. For example, the sample can be contacted with the detector probe prior to its contact with the immobilized capture probe in the lumen of the fractionation chamber. Alternatively, the sample and the detector probe can be independently contacted with the capture probe in the lumen of the fractionation chamber, or the sample can be contacted with the capture probe in the lumen of the fractionation chamber prior to the detector probe.

The capture probe for use in the method of the invention can contain the first member of a specific binding pair, and the separation step can be carried out by contacting the complex with the second member of the specific binding pair, which is immobilized on a solid support (e.g., an agarose or glass bead or a support in the lumen of a fractionation chamber, such as a capillary tube). The specific binding pair can be, e.g., a pair of complementary nucleic acids, a pair of polypeptides that specifically bind to one another (e.g., a polypeptide containing an antigen binding site of an antibody (in the context of, e.g., an antibody, such as a single chain antibody) and an antigen to which the antigen binding site binds), or avidin and biotin.

The capture probe used in the method of the invention can be immobilized in the lumen of a fractionation chamber (e.g., a capillary tube or a groove in the surface of a plate) and the isolating, releasing, and concentrating steps can thus be carried out in the lumen of the fractionating chamber.

Target analytes that can be detected using the method of the invention include, e.g., nucleic acids (e.g., a chromosome containing a translocation, or a pre-mRNA or mRNA transcript thereof), polypeptides, carbohydrates, lipids, metabolites, and drugs. The capture probes and detector probes can be, e.g., nucleic acids or polypeptides (e.g., a polypeptide containing an antigen binding site of an antibody, such as a single chain antibody).

The moiety can be released from the detector probes using methods including, e.g., chemical cleavage. For example, in the case where the moiety is linked to the detector probe by a disulfide bond, the moiety can be released by reduction of the disulfide bond. The moiety may also be released by enzymatic cleavage, e.g., by the use of a restriction enzyme, DNAse, RNAse, or a ribozyme.

In a second aspect, the invention features a method for detecting the presence of a chromosome containing a chromosomal translocation (i.e., a chromosome containing a portion of a first chromosome and a portion of a second chromosome) in a sample. In this method, the sample is contacted with a capture probe and a detector probe to form a detector probe-analyte-capture probe complex. The capture probe binds to the portion of the first chromosome, or a corresponding RNA transcript thereof, and contains the first member of a specific binding pair. The detector probe binds to the portion of the second chromosome, or a corresponding RNA transcript thereof, and contains a detectable label. The complex is then isolated from any detector probe that is not bound in the complex by contacting the complex with the second member of the specific binding pair, immobilized on a solid support. The detectable label present in the complex can then be detected as a measure of the presence of the chromosome containing the chromosomal translocation in the sample.

The invention also features probes (e.g., nucleic acid or polypeptide (e.g., antibody) probes) containing releasable moieties, which contain labels and have properties (e.g., predetermined pIs) that facilitate their isolation and/or concentration.

The invention provides several advantages, as it permits simultaneous analysis of multiple analytes in a sample on a micro-scale with high sensitivity. When using IEF analysis of a moiety released from an analyte-bound probe, the method of the invention avoids the need for empirical determination of the pi of an analyte-probe complex for each analyte to be detected. Moieties having predetermined pIs can be attached to probes specific for any analyte of interest. Similarly, when isolating the moieties based on size or mass, moieties having predetermined sizes or masses are attached to specific probes. The method of the invention also requires only small sample and reagent volumes, and is rapid and readily adaptable to automation. In addition, amplification by physical concentration of a moiety (e.g., by IEF or column chromatography) avoids background problems inherent in many detection methods employing enzymatic amplification (e.g., PCR).

Unless otherwise defined, all technical and scientific terms used herein have the same meaning as commonly understood by one of ordinary skill in the art to which this invention belongs. Although methods and materials similar or equivalent to those described herein can be used in the practice or testing of the invention, some preferred methods and materials are described below. All publications, patent applications, patents, and other references mentioned herein are incorporated by reference in their entirety. In case of a conflict, the present specification will control. In addition, the described materials, methods, and examples are illustrative only and are not intended to be limiting.

Other features and advantages of the invention will be apparent from the following detailed description and the claims.

DETAILED DESCRIPTION

The invention provides methods for detecting the presence of a target analyte in a sample. The methods of the invention employ a detector probe labeled with a moiety that (1) contains a detectable label, and (2) has a property (e.g., a predetermined pI) that facilitates its isolation and/or concentration. After the detector probe is bound to the target analyte to form a detector probe-analyte complex, and the complex is purified from sample components and unbound detector probe, the moiety is released from the complex and isolated and/or concentrated using methods appropriate for the specific moiety. For example, in the case of a moiety having a predetermined pI, the moiety is isolated and concentrated in a pH gradient by IEF. Detection of such a moiety at a position in the pH gradient corresponding to its pI is used as a measure of the presence and concentration of the target analyte in the sample.

The methods of the invention are described below with reference to the use of a labeled moiety having a predetermined pI. However, the invention can also be carried out using a labeled moiety having other properties that facilitate its isolation and/or concentration. Methods for isolating and concentrating moieties based on other properties, including, e.g., size, are well known in the art and include, e.g., column chromatography. A molecular sieve can also be used to isolate and/or concentrate moieties having different molecular weights. For example, a stack of filters, having progressively smaller pore sizes, can be used. In addition, the moieties can contain paramagnetic particles, which can be isolated and concentrated by exposure to a magnetic field. In order to use such moieties in a multiplex assay, the moieties can be, e.g., attached to their respective probes by different types of linkers, and thus released sequentially from the detector probes for isolation and concentration.

Hybridization Assays

Figure 1:
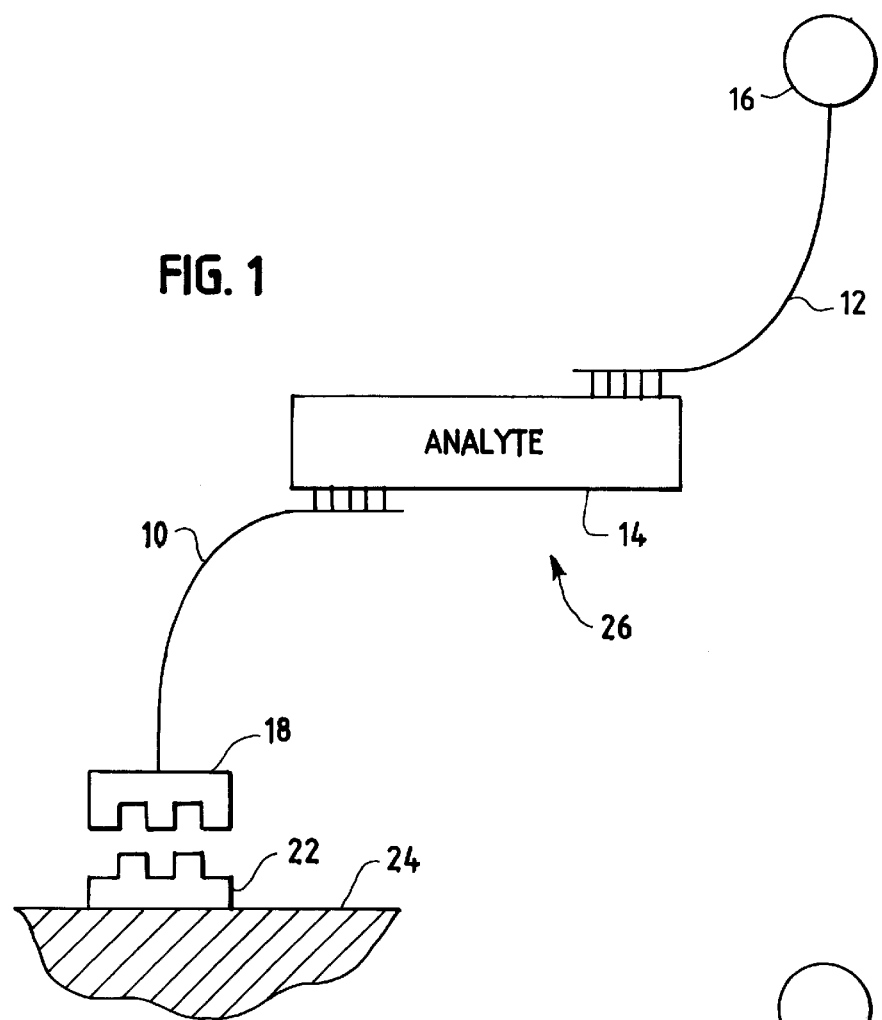
FIG. 1 is a schematic representation of a capture probe-analyte-detector probe complex, in which the capture probe contains the first member of a specific binding pair.
Figure 2:
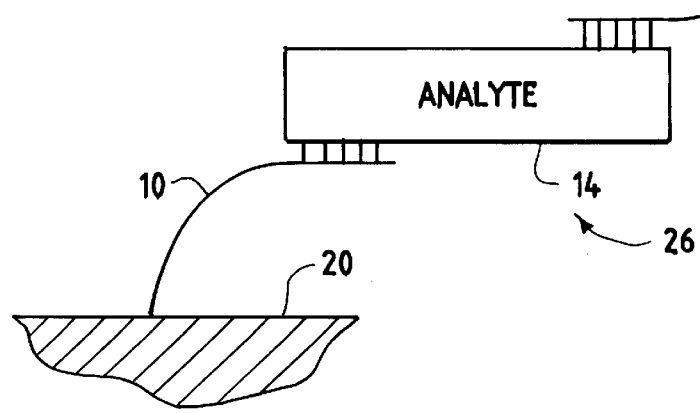
FIG. 2 is a schematic representation of a capture probe-analyte-detector probe complex, in which the capture probe is bound to a solid support.

Hybridization of a single probe to a target analyte to form an analyte-probe complex is carried out using standard methods. Alternatively, two probes, e.g., in the context of a sandwich hybridization assay, can be used (see, e.g., Ranki et al., Gene 21:77–85, 1983; U.S. Pat. No. 4,486,539 (1984)). As illustrated in FIGS. 1 and 2, sandwich hybridization assays involve the use of a capture probe 10 and a detector probe 12, which are designed to bind concurrently to a target analyte 14. In the context of the present invention, the detector probe 12 used in a sandwich hybridization assay includes a moiety 16, which, as described herein, contains a detectable label and has a predetermined pI or other known characteristics that allow the moiety to be isolated and/or concentrated. The capture probe can, e.g., (1) contain the first member of a specific binding pair 18 (FIG. 1), or (2) be immobilized on a solid support 20 (e.g., on a dipstick or on a solid support in the lumen of a fractionation chamber, such as a capillary tube) (FIG. 2). In either of these cases, use of the capture probe facilitates purification of the analyte-probe complex 26 from sample components, as well as from unbound detector probes. The sample can be contacted with the detector and capture probes simultaneously, or in sequence.

As shown in FIG. 1, when a capture probe 10 containing the first member of a specific binding pair 18 is used in a sandwich hybridization assay, the detector probe-analyte-capture probe complex 26 can be purified by contact with the second member of the specific binding pair 22, bound to a solid support 24. For example, the second member of the specific binding pair can be immobilized on a bead, such as a glass or an agarose bead. Contact of the sample with the bead will immobilize the complex on the bead. As is known in the art, binding of the detector probe-analyte-capture probe complex to such beads can be promoted by, e.g., continuous mixing of the sample and probes with the beads.

The beads can then be washed to remove unbound probe and non-specifically bound sample components. The moiety 16 can then be released from the purified complexes, and applied to a fractionation chamber, such as a capillary tube, for concentration, e.g., by IEF.

The second member of the specific binding pair 22 can also be immobilized on a solid support 24, such as a dipstick, or in the lumen of a fractionation chamber, for example, on the wall of the lumen of a capillary tube, or on a matrix, which can be made of any standard column-packing material (e.g., glass microbeads, agarose beads, glass wool, or a gel, such as a polyacrylamide gel), contained within such a chamber. As an example, the specific binding pair can be a pair of complementary oligonucleotides, e.g., poly-A and poly-T oligonucleotides. This configuration enables the use of a single capillary tube, for example, a capillary tube 24 containing immobilized poly-A 22, with any set of capture and detector probes, provided that the capture probe 10 contains a poly-T binding region 18.

Optimal lengths and levels of complementarity of oligonucleotides for use as specific binding pairs can be readily determined by one skilled in the art, and can vary depending on factors including sequence composition, sample complexity, and assay conditions (e.g., ionic strength, the types of salts used, the presence of organic solvents, and/or hybridization temperature). In the case of homopolymeric oligonucleotides (e.g., poly-A, poly-T, poly-G, and poly-C), for example, the first member of the specific binding pair, which is a component of the capture probe, can be, e.g., 8–100, 16–60, or 18–50 nucleotides in length. The second member of the specific binding pair, which is immobilized on the solid support (e.g., on a dipstick or in the lumen of a fractionation chamber), should be at least 8 nucleotides in length, but preferably is much longer, for example, 16–50, 18–100, or up to several hundred or several thousand nucleotides in length. Such lengthy homopolymeric oligonucleotides are made using standard methods, for example, by the use of terminal transferase.

In the case of pairs of heteropolymeric oligonucleotides, the first and second members of the specific binding pair can be, e.g., 8–100, 16–50, or 18–40 nucleotides in length. The second members of the specific binding pairs, for both homopolymers and heteropolymers, can be attached to the solid support by a linker, for example by a flexible carbon chain, such as a 3-glycidoxypropyltrimethoxysilane linker (see, e.g., Maskos et al., Nucl. Acids Res. 20(7):1679–1684, 1992).

The capture probe itself can also be immobilized in the lumen of a fractionation chamber (e.g., a capillary tube), either on the wall of the lumen or on a matrix, which can be made of any standard column-packing material (e.g., glass microbeads, agarose beads, glass wool, or a gel, such as a polyacrylamide gel) within the lumen. Methods for immobilizing probes (e.g., nucleic acid or protein probes) onto surfaces, such as glass or plastic surfaces, e.g., in the interior of a capillary tube, are well known in the art. For example, as mentioned above, oligonucleotides can be attached to a surface (e.g., a smooth or porous surface made of, e.g., glass, plastic (e.g., polypropylene), silicon, gold, or platinum) by the use of a linker, such as a 3-glycidoxypropyltrimethoxysilane linker (see, e.g., Maskos et al., supra).

The sample and the detector probe can be contacted with each other outside of such a fractionation chamber, then applied to the chamber as a mixture, or can be applied to the chamber individually, either simultaneously or sequentially. Formation of detector probe-analyte-capture probe complexes within the fractionation chamber can be facilitated by electrophoretic or physical (e.g., mechanical pumping) transfer of the target analyte from one end of the chamber to the other, each time passing immobilized capture probes to which it can bind. Once the complexes are formed, non-specifically bound sample components and unbound detector probes can be removed from the chamber by application of an electric field to the chamber, by physical washing, or by a combination of these methods. The moiety can then be released from the immobilized detector probes and focused by IEF. As described further below, multiple capture probes, specific for multiple target analytes, can be immobilized at random positions in the lumen of a single capillary tube. Such configurations facilitate detection of multiple target analytes in a single assay, depending on the use of an isoelectrically distinct moiety for each detector probe.

In addition to the sandwich hybridization assays described above, other standard hybridization methods employing the use of, for example, dipsticks or a single, labeled probe can be used in the method of the invention. Dipsticks can be used, for example, by serving as the solid support to which multiple capture probes are bound. Detector probe-analyte-capture probe complexes can thus be formed on the dipstick, and moieties released from the purified complexes can be fractionated by IEF, as described below. The dipstick can also contain an immobilized member (e.g., a poly-A tract) of a specific binding pair that binds to its cognate binding partner (e.g., a poly-T tract), present on a capture probe (see above). This type of configuration permits the use of a dipstick containing only one species of immobilized probe to be used in conjunction with capture probes specific for multiple analytes.

Target Analytes

Target analytes that can be detected using the methods of the invention include, e.g., nucleic acids, proteins, carbohydrates, lipids, metabolites, vitamins, and drugs. Detection of such molecules can be useful in fields such as medicine, forensics, agriculture, industry, food sciences, and veterinary medicine. For example, in the field of medicine, the methods of the invention can be used in the diagnosis of conditions (e.g., cancer) characterized by the presence or absence of specific markers (e.g., protein or nucleic acid markers) and/or altered levels of normally occurring proteins (e.g., hormones, cytokines, lymphokines, antibodies, or enzymes) or nucleic acids. The methods of the invention can also be used to detect gene mutations, which can be characterized by, e.g., single base pair changes, small or large deletions, insertions, or rearrangements (e.g., chromosomal translocations as described below), and genetic polymorphisms. In addition, the methods of the invention can be used to detect the presence of an infectious pathogen (e.g., a bacterium, virus, protozoan, parasite, or fungus) in a sample, e.g., a sample from a patient. Samples that can be tested using the methods of the invention include, e.g., biological fluids, such as blood, serum, plasma, urine, and saliva, as well as plant extracts, cell extracts, cell culture media, and fermentation mixtures. If necessary, protein and/or nucleic acid preparations can be prepared from the samples using standard methods, before application of the present methods. As discussed below, due to the sensitivity of the method, only small amounts of a sample are required for carrying out the methods of the invention.

Probes

The types of specific probes used in the invention depend on the particular type of target analyte to be detected, and are well known in the art. For example, in the case of a nucleic acid target (e.g., a DNA or an RNA target), nucleic acid probes can be used. The nucleic acid probes can contain deoxyribonucleotides, ribonucleotides, or combinations or modifications thereof. The optimal sequences, lengths, and levels of complementarity with the target analyte, in order to achieve specific binding, are parameters that are readily determined by those skilled in the art. For example, the probes can contain at least 8, for example 16–100 or 18–40, consecutive nucleotides that are complementary to the target nucleic acid analyte. The design of such probes can be facilitated by reference to standard protocol manuals and publicly available computer programs (see, e.g., Ausubel et al., eds. *Current Protocols in Molecular Biology,* Wiley & Sons, New York, 1989). Synthesis of nucleic acid probes can be carried out using standard chemical or recombinant methods. Alternatively, nucleic acid probes can be purchased from commercial vendors. The nucleic acid probes can be single-stranded or can contain single-stranded and double-stranded regions. In addition to nucleic acid probes, nucleic acid target analytes can be detected using polypeptide probes, for example, probes that contain nucleotide sequence-specific nucleic acid binding domains.

In the case of protein targets (e.g., antibodies, hormones, enzymes, pathogen proteins, cytokines, and lymphokines), antibodies, such as monoclonal antibodies that specifically bind to the analyte, can be used in the invention. Techniques for producing antibodies are well known in the art (see, e.g., Harlow et al., *Antibodies, A Laboratory Manual,* Cold Spring Harbor Laboratory Press, Cold Spring Harbor, New York, 1988). Particularly useful antibody molecules include Fab fragments of immunoglobulins, as well as recombinantly made single chain antibodies (see, e.g., Huston et al., U.S. Pat. Nos. 5,091,513 (1992) and 5,132,405 (1992); and Ladner et al., U.S. Pat. Nos. 4,704,692 (1987) and 4,946,778 (1990)). In addition to antibodies, non-antibody proteins and nucleic acids that specifically bind to target protein analytes can be used.

As mentioned above, capture probes used in the method of the invention can, e.g., (1) contain the first member of a specific binding pair, or (2) be immobilized on a solid support (e.g., on a dipstick or on a solid support in the lumen of a fractionation chamber, such as a capillary tube). Binding pairs that can be used in conjunction with capture probes include, e.g., streptavidin-biotin, as well as antibody-antigen, enzyme-substrate, receptor-ligand (e.g., hormone), nucleic acid-nucleic acid binding protein, and nucleic acid-nucleic acid binding pairs, and other specific binding pairs known in the art. The second member of the binding pair is immobilized on a solid support, such as an agarose bead or a glass microbead, using standard methods, or such a complex can be purchased from a commercial vendor. Immobilization of capture probes to, e.g., the lumen of a fractionation chamber or glass microbeads, which can be contained within the fractionation chamber, is described above. Detector probes used in the method of the invention contain moieties, which are described below.

Moieties

As mentioned above, detector probes used in the invention include a moiety that (1) contains a detectable label (e.g., a fluorescent, phosphorescent, radioactive, luminescent, or colored label), and (2) has a property that allows its isolation and/or concentration, e.g., a predetermined pI. The moiety can be a single molecule having both of these properties, or a complex of two or more molecules that together provide the moiety with these properties. The moiety can be a naturally occurring molecule or can be chemically synthesized. For example, the moiety can be a protein, peptide, protein complex, nucleic acid, carbohydrate, organic molecule, or a modification or combination thereof. Labels that can be used with the moiety include, e.g., fluorescent labels (e.g., fluorescein, rhodamine, or Texas Red), mixtures of fluorescent labels, chromophores, phosphorescent agents, and luminescent agents.

Specific examples of moieties that can be used in the invention include, e.g., members of the phycobilliprotein family (e.g., phycoerythrin and allophycocyanin), Starburst Dendrimers (Sigma Chemical, St. Louis, Mo.), an FITC coupled to a small amino acid chain (e.g., an amino acid chain containing a proteolytic cleavage site), and fluorescent dextrans (Molecular Probes, Eugene, OR; e.g., a dextran microparticle of several nanometers diameter covered with, e.g., a fluorophore; the microparticle can be linked to a detector probe by a polystyrene spacer-arm containing a cleavable bridge, such as a disulfide bond). Other examples of suitable moieties and chemical linkages can be found, e.g., in Haugland, "Handbook of Fluorescent Probes and Research Chemicals," Molecular Probes, Inc., Eugene, Oreg., 1992.

Streptavidin-phycoerythrin conjugates are extremely sensitive labels, as their fluorescence yield/molecule ratio is roughly equivalent to that of 100 rhodamine molecules or 30 fluorescein molecules. A commercially available streptavidin-phycoerythrin conjugate (Molecular Probes, Eugene, OR) focuses into multiple, discrete peaks having acidic pIs. Thus, streptavidin-phycoerythrin is a source for the isolation of numerous, distinct moieties having discrete pIs. The streptavidin-phycoerythrin can be fractionated by IEF in, e.g., a narrow pH gradient, and peaks corresponding to species having discrete pIs can be pooled for use as separate moieties.

Moieties having discrete pIs can also be obtained by chemical treatment. For example, treatment of streptavidin-phycoerythrin with water soluble carbodiimide/N-hydroxysulfosuccinimide(NHS)/ethylene diamine (see below) results in the production of a multiplicity of streptavidin-phycoerythrin products containing ethylene diamine, which increases the pIs of the proteins. These products have pIs in the range of 6–9, and can be fractionated into distinct species for use as moieties. Modified versions of moieties, e.g., phycoerythrin, can be made using these methods, or any other standard method in the art.

Moieties can be attached to detector probes using standard methods, which are selected based on the type of probe and moiety used. For example, molecules (e.g., protein or nucleic acid molecules) containing primary amines can be linked to molecules containing biotin and a disulfide bridge, e.g., as follows. The molecule containing the primary amine is reacted with an N-hydroxysulfosuccinimide (NHS) ester of biotin, that includes a disulfide bond in the spacer arm (e.g., EZ-Link NHS-SS-Biotin, Pierce Chemical Co., Rockford, Ill.), at or above neutral pH, resulting in covalent linkage of the molecule with SS-biotin and release of N-hydroxysulfosuccinimide. As a specific example of the use of such a modified molecule, an analyte-specific nucleic acid probe linked to SS-biotin can be linked with avidin-phycoerythrin to form a complete detector probe. Release of the moiety, after isolation of detector probe-analyte-capture probe complexes, can be achieved by contacting the complex with a reducing agent, such as dithiothreitol or β-mercaptoethanol.

Another well known coupling reaction involves reaction of a carboxyl group on one molecule with a primary amine on another molecule, in the presence of a carbodiimide coupling reagent, such as EDAC (1-ethyl-3-(3-dimethylaminopropyl) carbodiimide) (Biorad, Cambridge, Mass.). Reaction of these components results in a covalent linkage between the two molecules, accompanied by the release of urea. Moieties can also be introduced into detector probes as modified nucleotides during synthesis or after synthesis by chemical modification of nucleotides containing reactive groups, such as primary amines (see above).

In the case of a detector probe containing a nucleic acid segment between the analyte-binding region and the moiety (e.g., a nucleic acid probe), a nuclease can be used to release the moiety from the detector probe-analyte-capture probe complex. For example, a DNAse can be used to release moieties from probes containing DNA, while an RNAse (e.g., RNAse A or S1 nuclease) can be used to release moieties from probes containing RNA. Of course, such enzymes should not be used in cases where they adversely affect the integrity of the moiety.

In addition to enzymes such as DNAses and RNAses, enzymes having sequence specificity can be used to release moieties from detector probes. For example, the moiety can be linked to the probe by a single or double-stranded DNA sequence that contains a restriction endonuclease cleavage site. After isolation of the complex, the moiety can be released from the complex by incubation with the appropriate restriction endonuclease, using standard methods. With probes containing specific ribonucleotide sequences adjacent to the moiety, a ribozyme can be used to effect release.

Moieties can also be attached to detector probes (e.g., nucleic acid and polypeptide detector probes) by peptide linkages containing amino acid sequences that can be cleaved by sequence specific enzymes. For example, the moiety can be attached to the probe by a peptide having a sequence recognized by an enzyme, such as pyroglutamyl peptidase II (see, e.g., Wilk et al., Neurochem. Int. 15(1):81–89, 1989; Wilk et al., Neuropeptides 12:43–47, 1988; Wilk, Life Sciences 39:1487–1492, 1986; Charli et al., Neuropeptides 9:373–378, 1987). Such polypeptide probes can be made, e.g., using standard recombinant methods (see, e.g., Ausubel et al., supra).

Additional methods for linking moieties to probes are well known in the art, and include, e.g., the use of biodegradable ester linkers. For example, a palmitoyl residue can be linked to the 5' end of a nucleic acid probe by a bond that is cleavable by an esterase (see, e.g., Polushin et al., Nucleic Acids Res. 22:5492–5496, 1994). As is well known in the art, ester bridges can also be cleaved by increasing the pH from neutral to 9–10. Photochemical bridges that are cleaved by irradiation of specific wavelengths can also be used. Moieties can also be linked to detector probes by antibody-antigen and receptor-ligand interactions. For example, a labeled lectin that binds to a glycoconjugate, e.g., concanavalin A, which binds to $\alpha$-mannopyranosyl residues or $\alpha$-glucopyranosyl residues, can be used. In addition, moieties can be cross-linked to probes, such as polypeptide probes.

Isoelectric Focusing

Moieties cleaved from purified detector probe-analyte-capture probe complexes can be concentrated by IEF in a pH gradient to facilitate subsequent detection. The pH gradient can be created by application of an electric field to a mixture of ampholytes, which are compounds (e.g., low molecular weight polyamino-polycarboxylic acids or polymers of glycine, glycylglycine, amines, an epichlorohydrin) containing varying amounts of hydrogen-donating and hydrogen-accepting groups. In the presence of a charge gradient, the ampholytes migrate to their pIs, i.e., to the positions between the positive and negative poles where their net charges are zero. The ampholytes can have closely spaced pI values and high conductivity, and thus can partition into smooth pH gradients upon application of an electric field.

Specific ampholytes can be selected, depending on the moiety or moieties to be fractionated. For example, shallow gradients, i.e., gradients with relatively small changes in pH per unit length, often are useful as they permit resolution of moieties having similar pIs. For example, pH gradients which span, e.g., less than 2.0 pH units can be used. Such gradients permit resolution among members of a family of closely related chemical structures, and can be readily prepared by, e.g., fractionating conventional ampholyte mixtures to obtain preparations having a narrow pH range. It is often useful to prepare a gradient so that its ends have regions of constant pH that are fairly close to the predetermined pI of the moiety. For example, a gradient for detecting a moiety of pI 8.2 can extend from pH 7.7 to pH 8.7. This design can be used to eliminate charged species in the sample having pIs outside the range of the gradient. Such species rapidly migrate to the poles. Ampholytes are available from several commercial suppliers, such as Bio-Rad (Cambridge, Mass.) and Pharmacia Biotech. (Piscataway, N.J.).

Capillary Electrophoresis

IEF for use in the invention can be carried out in an elongated channel, such as a capillary tube, which is made of glass, plastic, or other material, and has an internal diameter of, for example, less than about 1 millimeter, e.g., less than 500 microns. For example, a capillary tube having an internal diameter of 100 microns and a length of 50 millimeters can be used. The surface area of such a capillary tube would allow the binding of on the order of $10^{13}$ capture probes. Higher surface to volume ratios can be achieved by using thinner and/or longer capillaries, thereby facilitating even more rapid hybridization kinetics. Methods for carrying out capillary IEF are well known in the art and are described, e.g., by Karger et al. (J. Chromatography, 492:585–614, 1989) and Novotny et al. (supra).

The use of a capillary tube, which has a high surface area to volume ratio, and thus a high capacity for dissipating heat, allows high voltages to be used in IEF methods, thus improving and accelerating the resolution of the moiety at its pI. In conventional IEF, electric fields on the order of 100 V/cm are generally used, while in capillary IEF, electric fields on the order of 200–500 V/cm can be used. Thus, IEF assays can be conducted rapidly, e.g., in a few minutes or seconds. In addition, in the case where capillary tubes containing immobilized capture probes are used, the high surface area to volume ratio of the capillary tubes facilitates target analyte hybridization to the capture probes, as any target molecule that passes through the capillary is in close proximity to the capture probes.

Another consequence of the high surface area to volume ratio of capillary tubes with respect to the present invention is that only very small quantities of reagents and test samples are required. For example, since only a few hundred fluorophores are needed for detection by a charge-coupled device (CCD; see, e.g., Mackay et al., U.S. Pat. No. 4,874, 492 (1989)), after fluorescence induction by a laser, a single milliliter of blood, which contains approximately $10^6$–$10^7$ white blood cells, should provide a sufficient amount of target for detection using the method of the invention. In the case where bacterial rRNAs are the target analytes, a single bacterium in a one milliliter sample should be detectable using the method of the invention.

Any of several standard capillary electrophoresis systems can be used to carry out the method of the invention. For example, the Beckman P/ACE System 2050 (Beckman Instruments, Columbia, Md.) can be used. In addition, systems that facilitate simultaneous processing of several capillary tubes can be used (see, e.g., Yeung et al., U.S. Pat. No. 5,324,401 (1994)).

In addition to capillary IEF, other IEF methods can be used in the invention. For example, IEF can be carried out in a groove etched into a plate, such as a glass or a plastic plate. In this method, each end of the groove is in contact with a well into one of which the sample is applied. Use of this type of system allows analysis of larger sample volumes. In addition, methods in which ampholytes are provided in a polyacrylamide gel support matrix, e.g., in an elongated horizontal slab gel or in a tube gel, can be used.

Detection of Focused Moieties

The emission, absorbance, or other detectable signal of a focused moiety can be detected using any of several standard methods, depending on the nature of the moiety. For example, a spectrophotometer can be used for detecting ultraviolet or x-ray irradiation of a moiety. A fluorescent moiety can be detected with a CCD device. A standard mercury light source, or a laser beam, can be used for excitation of the moiety, and a CCD device, such as a linear CCD device, can be employed for detection. The light source (e.g., a laser) can direct light perpendicularly to the moieties to be excited, or can be connected by a fiber optic cable in series with the capillary tube, so that the capillary tube itself is used as a light tunnel. In the case of an isotopically labeled moiety, a CCD device can be used to measure gamma irradiation directly. As will be apparent to one skilled in the art, appropriate filters, to remove scattered or reflected light, can be used with a detector device, such as a CCD device or a photomultiplier tube.

The detector can be positioned to specifically monitor the precise location in the pH gradient corresponding to the pI of the moiety. Alternatively, the detector can be moved along the pH gradient, or the chamber containing the gradient (e.g., a capillary tube) can be moved past a detector. In another example, neither the capillary, nor the detector is moved. Rather, once the moiety is focused, it is transported within the capillary tube so that it moves past a detector. Such transport can be induced, e.g., by pumping fluid through the capillary to convectively move the gradient. In any example where the plug or zone of complex is moved relative to the detector, the predetermined pI will remain constant, but the physical position of the focused moiety will shift. In a device where the whole gradient is moved, the detector can be programmed to take a reading only at a predetermined time after the start of flow, such as the time determined to coincide with passage of the moiety. Also, a linear CCD device, spanning the length of the fractionation chamber, can be used. Appropriate systems integrating signal induction (e.g., lasers) and detection (e.g., CCD devices) devices are well known in the art (see, e.g., Fujimiya et al., U.S. Pat. No. 5,069,769 (1991); Pentoney, U.S. Pat. No. 5,208,466 (1993)).

To conduct a quantitative analysis of a target analyte, a standard curve can first be prepared, using standard methods. For example, the amount of label detected using the method of the invention can be determined for several samples containing known quantities of analyte. A standard curve generated by these readings can then be used to determine the concentration of the analyte in a sample having an unknown analyte concentration, by comparing the level of the signal detected to the standard curve.

Detection of Multiple Analytes in a Sample

An advantage of the invention is that it facilitates detection of multiple analytes in a sample using a single pH gradient. For example, probes specific for several analytes, each containing isoelectrically distinct moieties, can be used together in the same assay. After hybridization, capture, moiety release, and IEF, the different moieties are detected at their unique positions in the pH gradient, as a measure of the presence of each analyte in the sample. In an assay for multiple analytes in a single pH gradient, it is necessary only that each moiety corresponding to a different target analyte has a unique and distinguishable pI in the gradient, i.e., the detectable label can be the same on each otherwise distinct moiety. The number of simultaneous detections (i.e., the number of different probes) that can be carried out is limited only by the resolution of the detection device and/or the ability to resolve the moieties during IEF.

EXAMPLE I—Detection of Salmonella in a Biological Sample

The methods of the invention can be used to detect the presence of a pathogenic organism in a sample, for example, Salmonella in a food sample. Reagents and methods adaptable for carrying out this assay are provided in the GENE-TRAK Salmonella Assay Kit (GENE-TRAK Industrial Diagnostics, Hopkinton, Mass.). Briefly, a genosensor (a dipstick in the GENE-TRAK assay, but a capillary tube can also be used) coated with a poly-A probe is contacted with a sample, a capture probe, which contains a poly-T tail, and a detector probe. The detector probe is designed to contain a moiety of the invention, such as a streptavidin-phycoerythrin moiety. A specific example of a detector probe that can be used in this method is as follows: phycoerythrin-streptavidin-biotin-SS-AmT-AGCTCACAGCATATGCGCTTTTGTGTAC-3' (SEQ ID NO:1), where AmT is an amino modifier, $C_6dT$, which is a thymidine that contains a primary amine attached via a 6-carbon linker. After washing to remove non-specifically bound material, including unbound detector probes, the dipstick is transferred to a tube containing a 1–2% solution of ampholytes and a releasing agent (e.g., in the case of the specific probe described above, a reducing agent (e.g., dithiothreitol or P-mercaptoethanol) is used to cleave the disulfide bond, resulting in the release of S-biotin-streptavidin-phycoerythrin). After removal of the moiety from the complex, the solution is transferred to an IEF tube, to which a current is applied to establish a pH gradient. The moiety is then detected at the position in the pH gradient corresponding to its pI, as described above.

EXAMPLE II—Detection of Chromosomal Translocations

The invention can be used to detect chromosomal translocations. As a specific example, the method can be used to detect the so-called "Philadelphia" chromosome, the presence of which is the underlying cause of acute lymphocytic leukemia and chronic myelogenous leukemia. The Philadelphia chromosome is characterized by having a balanced translocation of the terminal region of chromosome 9 to the terminal region of chromosome 22. This results in a gene fusion between the abl oncogene on chromosome 9 and the bcr gene on chromosome 22. This gene fusion is transcribed into a message containing regions corresponding to both genes.

The present invention can be used to detect such translocations as follows. A capture probe can be designed to hybridize to the bcr region of the fusion (either the gene itself or an RNA (pre-mRNA or mRNA) transcript thereof), while a detector probe can be designed to hybridize to the abl region. Capture of the abl detector probe by the bcr capture probe indicates the presence of the Philadelphia translocation.

Other Embodiments

It is to be understood that, while the invention has been described in conjunction with the detailed description thereof, the foregoing description is intended to illustrate and not limit the scope of the invention. Other aspects, advantages, and modifications of the invention are within the scope of the following claims.

---

---

What is claimed is:

1. A method for detecting an analyte in a sample, said method comprising the steps of:
   contacting said sample with a detector probe and a capture probe to form a detector probe-analyte-capture probe complex, wherein said detector probe comprises a moiety having a predetermined pI and comprising a detectable label;
   separating said complex from any detector probe that is not bound in said complex;
   releasing said moiety from said complex;
   isolating said moiety released from said complex and concentrating said moiety by isoelectric focusing; and
   detecting said moiety as a measure of the presence of said analyte in said sample.

2. The method of claim 1, wherein
   said detecting of said moiety as a measure of the presence of said analyte in said sample is carried out by detecting said concentrated moiety at a position in a pH gradient corresponding to said pI of said moiety.

3. The method of claim 1, wherein said isolating is carried out by the use of column chromatography or a molecular sieve.

4. The method of claim 1, wherein said capture probe is immobilized in the lumen of a fractionation chamber and said isolating, releasing, and concentrating steps are carried out in said lumen.

5. The method of claim 4, wherein said sample is contacted with said detector probe prior to its contact with said immobilized capture probe in said lumen.

6. The method of claim 4, wherein said sample and said detector probe are independently contacted with said capture probe in said lumen.

7. The method of claim 6, wherein said sample is contacted with said capture probe in said lumen prior to said detector probe.

8. The method of claim 1, wherein said capture probe comprises a first member of a specific binding pair and said separation step is carried out by contacting said complex with a second member of said specific binding pair, wherein said second member of said specific binding pair is immobilized on a solid support.

9. The method of claim 8, wherein said solid support is in the lumen of a fractionation chamber.

10. The method of claim 8, wherein said specific binding pair comprises a pair of complementary nucleic acids.

11. The method of claim 8, wherein said specific binding pair comprises a pair of polypeptides that specifically bind to one another.

12. The method of claim 11, wherein said first member of said specific binding pair comprises an antigen binding site of an antibody and said second member of said specific binding pair comprises an antigen to which said antigen binding site binds.

13. The method of claim 8, wherein said first member of said specific binding pair comprises avidin, and said second member of said specific binding pair comprises biotin.

14. The method of claim 1, wherein said isoelectric focusing is carried out in the lumen of a capillary tube.

15. The method of claim 1, wherein said isoelectric focusing is carried out in a groove in the surface of a plate.

16. The method of claim 1, wherein said analyte comprises a nucleic acid.

17. The method of claim 16, wherein said analyte comprises a chromosome comprising a translocation, or a pre-mRNA or mRNA transcript thereof.

18. The method of claim 1, wherein said detector probe comprises a nucleic acid.

19. The method of claim 1, wherein said capture probe comprises a nucleic acid.

20. The method of claim 1, wherein said analyte comprises a polypeptide.

21. The method of claim 1, wherein said analyte comprises a carbohydrate, lipid, metabolite, or drug.

22. The method of claim 1, wherein said detector probe comprises a polypeptide.

23. The method of claim 22, wherein said polypeptide comprises an antigen binding site of an antibody.

24. The method of claim 23, wherein said polypeptide comprises a single chain antibody.

25. The method of claim 1, wherein said capture probe comprises a polypeptide.

26. The method of claim 25, wherein said polypeptide comprises an antigen binding site of an antibody.

27. The method of claim 26, wherein said detector probe comprises a single chain antibody.

28. The method of claim 1, wherein said releasing step is carried out by chemical cleavage.

29. The method of claim 28, wherein said moiety is linked to said detector probe by a disulfide bond and said releasing step is carried out by reduction of said disulfide bond.

30. The method of claim 1, wherein said releasing step is carried out by enzymatic cleavage.

31. The method of claim 1, wherein said moiety comprises phycoerythrin, or a modified version thereof.

32. A method for detecting the presence of a chromosome comprising a chromosomal translocation in a sample, wherein said chromosome comprises a portion of a first chromosome and a portion of a second chromosome, said method comprising the steps of:

contacting said sample with a capture probe and a detector probe to form a detector probe-analyte-capture probe complex, wherein said capture probe binds to said portion of said first chromosome, or a corresponding RNA transcript thereof, and comprises the first member of a specific binding pair, and said detector probe binds to said portion of said second chromosome, or a corresponding RNA transcript thereof, and comprises a moiety having a predetermined pI and a detectable label;

separating said complex from any detector probe that is not bound in said complex by contacting said complex with the second member of said specific binding pair, said second member being immobilized on a solid support;

releasing said moiety from said complex;

concentrating said moiety by isoelectric focusing; and detecting the concentrated moiety as a measure of the presence of said chromosome containing said chromosomal translocation in said sample.

* * * * *